(12) United States Patent
Jinno et al.

(10) Patent No.: US 12,385,047 B2
(45) Date of Patent: Aug. 12, 2025

(54) TRANSFORMED CELL PRODUCTION METHOD

(71) Applicants: PEARL KOGYO CO., LTD., Osaka (JP); I-GENE CORPORATION, Tokyo (JP); NATIONAL UNIVERSITY CORPORATION EHIME UNIVERSITY, Ehime (JP)

(72) Inventors: Masafumi Jinno, Ehime (JP); Hidemasa Kato, Ehime (JP); Yoshimi Tokuzawa, Ehime (JP); Akihito Onishi, Ehime (JP); Junko Myojo, Ehime (JP); Susumu Satoh, Ibaraki (JP)

(73) Assignees: PEARL KOGYO CO., LTD., Osaka (JP); I-GENE CORPORATION, Ehime (JP); NATIONAL UNIVERSITY CORPORATION EHIME UNIVERSITY, Ehime (JP)

( * ) Notice: Subject to any disclaimer, the term of this patent is extended or adjusted under 35 U.S.C. 154(b) by 1210 days.

(21) Appl. No.: 17/253,867

(22) PCT Filed: Jun. 18, 2019

(86) PCT No.: PCT/JP2019/024134
§ 371 (c)(1),
(2) Date: Dec. 18, 2020

(87) PCT Pub. No.: WO2019/244895
PCT Pub. Date: Dec. 26, 2019

(65) Prior Publication Data
US 2021/0269809 A1     Sep. 2, 2021

(30) Foreign Application Priority Data

Jun. 18, 2018   (JP) .................... 2018-115200

(51) Int. Cl.
*C12N 15/00*   (2006.01)
*C12N 5/00*    (2006.01)
*C12N 15/63*   (2006.01)

(52) U.S. Cl.
CPC ........... *C12N 15/63* (2013.01); *C12N 5/0018* (2013.01); *C12N 5/0081* (2013.01)

(58) Field of Classification Search
CPC .............. A61P 35/00; C07K 2317/732; C07K 2319/00; C12N 15/87; C12N 15/113; C12N 15/62; C12N 15/1137
USPC ..................................................... 435/6.16
See application file for complete search history.

(56) References Cited

U.S. PATENT DOCUMENTS

2004/0110297 A1   6/2004   Miyoshi et al.
2017/0226483 A1   8/2017   Abraham et al.

FOREIGN PATENT DOCUMENTS

| JP | 2010-220517 A | 10/2010 |
|---|---|---|
| JP | 2013-255474 A | 12/2013 |
| JP | 2013-255475 A | 12/2013 |
| JP | 2017-189158 A | 10/2017 |
| WO | 02/064767 A1 | 8/2002 |
| WO | 2004/015101 A1 | 2/2004 |
| WO | 2014/208425 A1 | 12/2014 |
| WO | 2017/123789 A1 | 7/2017 |

OTHER PUBLICATIONS

Witkowski et al., (Biochemistry 38:11643-11650, 1999.*
Kisselev L., (Structure, 2002, vol. 10: 8-9.*
Whisstock et al., (Quarterly Reviews of Biophysics 2003, vol. 36 (3): 307-340.*
Devos et al., (Proteins: Structure, Function and Genetics, 2000, vol. 41: 98-107.*
Jinno et al. "Investigation of plasma induced electrical and chemical factors and their contribution processes to plasma gene transfection," Archives of Biochemistry and Biophysics, 605: 59-66 (2016).
Jinno et al. "Synergistic effect of electrical and chemical factors on endocytosis in micro-discharge plasma gene transfection," Plasma Sources Science and Technology, 26 (6): 65016 (2017).
Edelblute et al. "Activated Air Produced by Shielded Sliding Discharge Plasma Mediates Plasmid DNA Delivery to Mammalian Cells," Biotechnology and Bioengineering, 112 (12): 2583-2590 (2015).
Extended European Search Report issued in counterpart European Patent Application No. 19822153.3 dated Feb. 21, 2022.
International Search Report issued in corresponding International Patent Application No. PCT/JP2019/024134 dated Sep. 3, 2019.
Kaneko et al., "29p-B7-4 Production of hydroxyl radical-controlled plasma and its application to gene transfer," Lecture preprints of the 60th JSAP Spring Meeting, 08-128 (Mar. 27, 2013).
Sato et al., "30p-L-5 Application of plasma technology to molecular biology—Research on molecular introduction into cells and tissues, and equipment development," Lecture preprints of the 56th conference of the Japan Society of Applied Physics and the Related Societies, The Japan Society of Applied Physics, p. 25 (Mar. 30, 2009).

* cited by examiner

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

Provided is a method for producing transformed cells, comprising an introduction step of contacting an introduction liquid comprising a molecule of interest with a target cell to introduce the molecule of interest into the target cell, wherein, in the introduction step, the molecule of interest is introduced via endocytosis into the target cell, a trait is conferred, deleted, or maintained by the introduction of the molecule of interest, and the molecule of interest such as a vector added exogenously does not then remain in an established cell.

17 Claims, 11 Drawing Sheets

Specification includes a Sequence Listing.

(A)

pCXLE-EGFP
PLASMID (10.9 kbp)-
INTRODUCED CELL (B)

pmCherry-C1
PLASMID (4.7 kbp)-
INTRODUCED CELL (A)

HDF CELLS (BEFORE INTRODUCTION)

(B)

iPS CELLS PRODUCED FROM HDF CELLS BY GENE INTRODUCTION USING CREEPING DISCHARGE (B)

(A)

(B)

(A)

(C)

TRANSFORMED CELL PRODUCTION METHOD

SEQUENCE LISTING SUBMISSION VIA EFS-WEB

A computer readable text file, entitled "SequenceListing.txt," created on or about Dec. 15, 2020 with a file size of about 2 kb contains the sequence listing for this application and is hereby incorporated by reference in its entirety.

TECHNICAL FIELD

The present invention relates to a method for producing transformed cells.

BACKGROUND ART

Examples of the known technique for introducing a molecule of interest such as a nucleic acid or a protein into cells include a biological technique using a virus, a physical technique such as electroporation or microinjection, a chemical technique such as lipofection, and a method using plasma (Patent Literature 1: Japanese Patent Laying-Open No. 2013-255475). In recent years, therapy, etc. have been about to be performed in which a molecule of interest is introduced into cells or tissues for advanced medicine such as regenerative medicine or gene therapy, the cells that acquire a new trait are established, and the cells are used.

CITATION LIST

Patent Literature

PTL 1: Japanese Patent Laying-Open No. 2013-255475

SUMMARY OF INVENTION

Technical Problem

However, it is known that when a molecule of interest is introduced using electroporation, pores are made in cell membranes, electroporation therefore has a high cytotoxic effect, and the molecule of interest is easily incorporated into damaged chromosomes in a repair process. Since the molecule of interest that remains in the cells causes the problem of deteriorating traits which the cells themselves hold or causing immunopathy or the canceration of the cells, the molecule of interest prevents the practical use of advanced medicine such as regenerative medicine or gene therapy. Even in the case of an introduction method using a virus and generally used as a method for introducing a molecule of interest, the cell type into which the molecule of interest can be introduced is limited, and an introduced nucleic acid and a viral vector used to introduce a gene may be incorporated into chromosomes.

Therefore, in order to establish, as practically usable medical technology, advanced medicine such as regenerative medicine or cell medicine using cells such as iPS cells on which a new trait is conferred, the establishment of a convenient method for producing transformed cells such as induced pluripotent stem cells (iPS cells) and differentiated cells using an introduction method in which a exogenous gene does not remain has been desired.

Therefore, an object of the present invention is to provide a method for producing transformed cells in which a molecule of interest introduced exogenously does not remain.

Solution to Problem

[1] A method for producing transformed cells, comprising: an introduction step of contacting an introduction liquid comprising a molecule of interest with a target cell to introduce the molecule of interest into the target cell, thereby producing a transformed cell in which a trait is conferred, deleted, or maintained by introducing the molecule of interest.

[2] The production method according to [1], wherein the molecule of interest is at least one selected from the group consisting of a nucleic acid and a protein.

[3] The production method according to [2], wherein the nucleic acid is a vector.

[4] The production method according to [3], wherein the vector expresses a protein that confers, deletes, or maintains the trait in the cell.

[5] The production method according to any one of [2] to [4], wherein the nucleic acid is not inserted into a chromosome in 80% or more of the transformed cells.

[6] The production method according to any one of [1] to [5], wherein in the introduction step, the molecule of interest is introduced via endocytosis into the target cell.

[7] The production method according to any one of [1] to [6], wherein in the introduction step, the molecule of interest is introduced by subjecting the target cell to creeping discharge or plasma treatment.

[8] The production method according to any one of [1] to [7], comprising: a post-culture step of culturing the target cell after the introduction step.

[9] The production method according to [8], wherein in the post-culture step, a culture medium for the target cell comprises a selective molecule that can kill a cell.

[10] The production method according to any one of [1] to [9], wherein the molecule of interest comprises a selective marker molecule having resistance to a selective molecule.

Advantageous Effects of Invention

According to the present invention, a method for producing a transformed cell in which a molecule of interest introduced exogenously does not remain can be provided.

DESCRIPTION OF EMBODIMENTS

Figure 1:
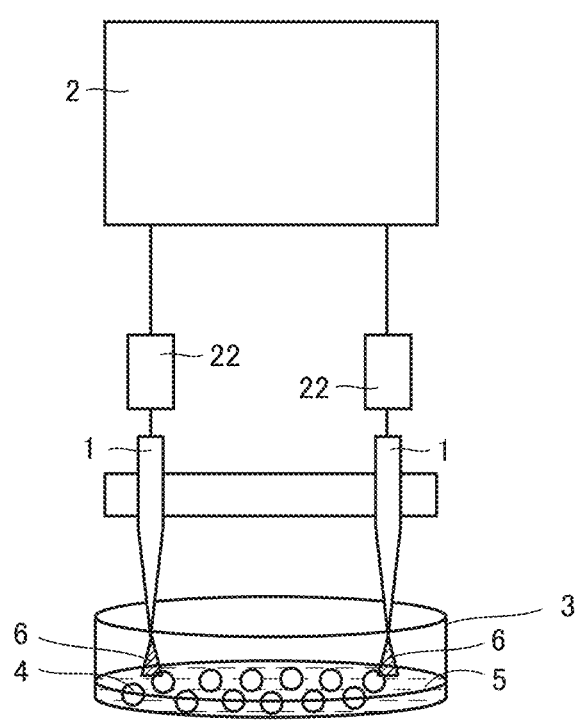
FIG. 1 is a schematic diagram describing one example of a device used for introducing of a molecule of interest.

Embodiments of the present invention will be described with reference to the figures hereinafter.

A production method of the present invention comprises: an introduction step of contacting an introduction liquid comprising a molecule of interest with a target cell to introduce the molecule of interest into the target cell, thereby producing a transformed cell in which a trait is conferred, deleted, or maintained by introducing the molecule of interest.

In the present invention, the transformed cell refers to a cell in which a trait is conferred, deleted, or maintained by introducing a molecule of interest. Examples of the transformed cell include a cell in which gene expression is changed, a cell the form of which is changed, a cell in which the enzyme activity is changed, and a cell in which the localization of molecules is changed. The transformed cell may be accompanied with mutation of the genome of the target cell, or may not be accompanied. The transformed cell may be accompanied with epigenetic mutations such as the methylation of DNA and the methylation and the acetylation of histone. Examples of the transformed cell on which a new trait is conferred include a cell in which one or more specific genes are expressed, a stem cell (including a pluripotent stem cell), a precursor cell, a dedifferentiated cell, and a differentiation-induced cell. Examples of the cell in which a trait is deleted include a cell in which the expression of one or more specific genes is suppressed and a cell in which a mutant gene is deleted from a cell having gene mutation. In addition, examples of the transformed cell include a cell in which a trait changes if no treatment is performed, and the trait is maintained with a molecule of interest and a cell in which a trait is deleted, and on which a trait is then conferred. Examples of the transformed cell also include a cell in which a causal gene is deleted from a stem cell of a patient with hereditary disease, and into which a normal gene is introduced. It can be determined whether a cell is a transformed cell by morphological observation through a microscope, a method for quantifying the amount of an RNA or a protein expressed, or a method that is well-known to those skilled in the art such as immunostaining.

The fact that, in a transformed cell, a molecule of interest does not remain means that, after culture for a certain period from the introduction of the molecule of interest, the amount of the molecule of interest measured by a well-known method is below a detection limit or below a certain detection value. Depending on the concentration and the stability of the molecule of interest in the target cell, after culture for, for example, 1 week, preferably 2 weeks or more from introduction, the cells may be cloned, and it may be confirmed whether the molecule of interest remains. When a nucleic acid is used as the molecule of interest, the fact that the molecule of interest does not remain means, for example, that the introduced nucleic acid is not inserted into a chromosome of the transformed cell. The fact that the molecule of interest is not inserted into a chromosome of the transformed cell means, for example, a case where the genome DNAs are extracted from the produced transformed cell, qPCR targeting the nucleic acid sequence of the molecule of interest is performed, and the relative amount of the molecule of interest when the number of copies of the genome DNAs is defined as 1 is 0.1 or less. The percentage of cells in which the nucleic acid is not inserted into the chromosome in the obtained transformed cells is preferably 80% or more, more preferably 90% or more, and most preferably 100%.

(Target Cell)

The target cell used in the production method of the present invention refers to a cell into which the molecule of interest is introduced, and is not limited to a specific type of cell. Specific examples of such a target cell include cells of animals including a human. Example of the animal cells include a cell constituting tissues (a fibroblast, an epidermal cell, a mammary cell, a fat cell, a myoblast, an osteoblast, a hepatic cell, a cardiac muscle cell, a vascular endothelial cell, precursor cells thereof, etc.), a cell of the immune system (a B cell, a T cell, a monocyte cell, etc.), a neuron, a stem cell (including a pluripotent stem cell, a blood stem cell, a mesenchymal stem cell, and a neural stem cell), and a tumor cell. The cell may be an adherent cell or a floating cell. The target cell can be obtained by purchase, for example, from culture collections or commercial makers such as ATCC, JCRB, and RIKEN BRC. A single type of these target cells may be used, or two or more different types may be mixed and used. The molecule of interest can also be introduced into a plurality of target cells simultaneously.

Examples of the target cell include cells collected from an individual organism body or tissue and cells in an individual organism body or tissue. Examples of the cell collected from an individual organism body or tissue include: a cell that is not presumed to be returned to an individual organism body and used for the R&D of a pharmaceutical agent, etc.; or a cell that is presumed to be returned to an individual organism body and used for regenerative medicine, etc. Examples of the cell collected from an individual organism body or tissue also include a cell cultured after collected from an individual organism body or tissue.

Examples of the target cell used in the invention include a prokaryotic cell from *E. coli*, actinomycetes, *Bacillus subtilis*, etc., or an eukaryotic cell such as a microbial cell such as yeast, an insect cell, a mammalian cell from a mouse, a rabbit, a rat, a goat, a dog, a simian, or the like, a plant cell, etc.

Furthermore, the target cell used in the invention may not be subjected to specific treatment and, in order to increase the efficiency of introducing a molecule of interest, may be subjected to treatment to prepare a competent cell, which is commonly used at the time of gene introduction. Specific examples include an *E. coli* competent cell that is treated with calcium chloride so as to change the structure of a cell membrane, so that the cell membrane is readily permeable to a DNA molecule.

In the present invention, examples of the target cell also include a target tissue, which is a target for introducing the molecule of interest. The tissue in the present invention is a unit of a structure in which several types of cells having different properties and functions gather in a certain form. The target tissue is not limited to a specific type of tissue. Specific examples of such a target tissue include: a tissue collected from the living body; a tissue in the living body; a donor-derived organ used for transplantation; a tissue reconstructed by culture; or a pre-differentiation plant tissue constructed by callus culture. Examples of the target tissue include a viviparous tissue, an embryonic tissue, a skin tissue, a bone tissue, a cartilage tissue, a muscular tissue, a fat tissue, a cardiac muscle tissue, a nervous system tissue, a lung tissue, a pancreas tissue, a liver tissue, a hair papilla tissue, a dental pulp, and a tumor tissue. A single type of these target tissues may be used, or two or more different types may be mixed and used. When a tissue is used as the target cell, a tissue on/in which a trait is conferred or deleted is produced by introducing the molecule of interest.

(Molecule of Interest)

In the present invention, the molecule of interest refers to a molecule which is an object introduced into the target cell, and is not particularly limited to a specific type of molecule, and the molecule of interest is preferably at least one selected from the group consisting of (a) a nucleic acid and (b) a protein.

(a) Nucleic Acid

Specific examples of the nucleic acid include a DNA, an RNA, other nucleic acid molecules, or derivatives thereof. The DNA or RNA may be a single strand or a double strand and may be linear or circular. The molecular weight of the nucleic acid is not particularly limited. Examples of the RNA include a messenger RNA (mRNA), a ribozyme, a small interfering RNA (siRNA), a small hairpin RNA (shRNA), a guide RNA (gRNA), an antisense RNA, and other non-coding RNAs. Examples of the nucleic acid may include a nucleic acid (DNA) transferred as these RNAs. In addition, the nucleic acid may include a nucleic acid (DNA or RNA) encoding the following protein. These nucleic acids may be introduced singly or in combinations of two or more.

The nucleic acid is preferably a vector. The vector is a medium of a nucleic acid molecule for amplifying, maintaining, and introducing a nucleic acid. In the present invention, the vector is preferably an expression vector, and a nucleic acid sequence that expresses an RNA or a protein of interest is inserted thereinto. As the expression vector, for example, a plasmid vector, a cosmid vector, a bacterial artificial chromosome (BAC), a yeast artificial chromosome (YAC), and other non-plasmid vectors can be used. The expression vector has a structure (sequence) for expressing an RNA or a protein efficiently. Examples of such a sequence include a promoter sequence, a Kozak sequence, a Shine-Dalgarno sequence, an intron, a spacer sequence, an enhancer sequence, a terminator sequence, and an internal ribosome entry site (IRES).

(b) Protein

Examples of the protein include a polymer compound such as peptide, polypeptide, or a derivative thereof in which amino acids are polymerized. Examples of the protein include, but are not particularly limited to, various well-known proteins, and include a signal-transmitting substance, a gene expression control factor (including transfer, translation, and transport), a DNA methylation regulatory factor, a histone modification regulatory factor, a factor used for genome editing, a structural protein, a growth factor, a hormone, an enzyme, a ligand, a receptor, an antibody or a Fab portion of an antibody, and a non-orally administrable protein pharmaceutical agent.

A protein introduced as an molecule of interest or a protein expressed from an introduced nucleic acid or an introduced vector is preferably a protein that confers, deletes, or maintains a trait on/in a cell, and more preferably a protein that confers, deletes, or maintains a constant trait on/in a cell by temporary expression. Examples of such a protein include a transcription regulatory factor (for example, SOX2, KLF4, L-Myc, OCT3/4, etc.), a translation regulatory factor (for example, Lin28, etc.), a DNA methylation regulatory factor (for example, TET1, etc.), a factor used for genome editing (for example, Cas9, etc.), and a growth factor (for example, activin, BMP4, etc.). These proteins may be introduced singly or in combinations of two or more.

Examples of another molecule of interest include a sugar, a lipid, a low-molecular-weight physiologically active substance, or a drug candidate. Among them, a physiologically active low-molecular-weight compound such as a pharmaceutical agent (for example, the molecular weight is 100 kDa or less) which is unlikely to be introduced into a tissue or a cell by other introduction methods is preferable. The low-molecular-weight compound that is unlikely to be introduced into a tissue or a cell by other introduction methods refers to a small molecule with a molecular weight of 1000 Da or higher, a molecule with low membrane permeability, or the like. A single type of the above-described respective molecules of interest may be used, or two or more different types may be mixed and used.

A genome editing system may be used as the molecule of interest. The genome editing system is a system that converts genetic information sequence-specifically, and enables the deletion of a base sequence, the substitution of an amino acid sequence, the introduction of a exogenous gene, etc. Examples of the genome editing system include a zinc finger nuclease (zinc-finger, ZFN), TALEN, CRISPR/Cas9, CRISPR/Cpf1, a meganuclease, a CAS9 nickase, and Target-AID, which enable sequence-specific DNA cleavage.

As a method for introducing a genome editing system into a cell, a method such as introducing a genome editing system in which a necessary gene is encoded in a virus into a cell by the infectivity of the virus or introducing a genome editing system in which a necessary gene is encoded in a plasmid into a cell by electroporation is commonly used.

Although the gene transfer efficiency is good in an introduction method using a virus, the introduction method has the following problems: (1) facilities in which experimental operation can be performed are limited, (2) a virus genome is introduced into a cell, (3) when a retrovirus, etc. are used, an introduced gene, etc. including a virus genome are integrated into a chromosome, and (4) cells that can be infected are limited depending on a virus to be used. An introduction method by electroporation has the following problems: (1) as many as $1\times10^6$ cells are necessary for implementation, the death rate of cells is high, and direct introduction into a cell derived from the living body or the living body is difficult, (2) a great decrease in transfer efficiency is observed depending on plasmid size, and (3) an introduced gene, etc. are integrated into a chromosome.

The fact that a gene other than a target gene is also mutated (off-targeting) is pointed out as the significant problem for genome editing technology, and is an inhibitor of the practical application to medicine, etc. As one of the causes for off-target, an introduced genome editing system, an introduced virus genome, the introduced DNA of a vector, etc. being integrated into a chromosome, and the genome editing system continuing to be constantly expressed in a cell are mentioned.

According to the present invention, a transformed cell in which a target gene is edited by introducing a genome editing system efficiently, and the genome editing system does not remain in the cell after the completion of genome editing can be obtained conveniently.

(Introduction Liquid)

Although the introduction liquid containing a molecule of interest is not particularly limited, the molecule of interest is preferably suspended in a suitable medium such as water, an aqueous solution, or a culture medium. Examples of a solvent or a dispersion medium for the aqueous solution or the suspension include a physiological saline solution and a pH buffer solution.

[Introduction Step]

In the introduction step of the present invention, an introduction liquid containing a molecule of interest is contacted with a target cell, and the molecule of interest is introduced into the target cell. The introduction of the molecule of interest into the target cell means, for example, that the molecule of interest enters a cytoplasmic matrix or a nucleus and can function. In the introduction step, the molecule of interest is preferably introduced via endocytosis into the target cell. It is because endocytosis is a function that an organism originally holds, and does not damage a cell membrane or a chromosomal gene unlike electroporation, and cytotoxic effects, and the denaturation and the recombination of the chromosomal gene can be suppressed. The introduction step comprises at least a step of contacting an introduction liquid containing a molecule of interest with a target cell.

<Step of Contacting Introduction Liquid Containing Molecule of Interest with Target Cell>

The step of contacting an introduction liquid containing a molecule of interest with a target cell preferably comprises a step of pre-culturing a target cell and a step of adding an introduction liquid containing a molecule of interest.

In the step of pre-culturing a target cell, a target cell is cultured under suitable conditions. The method for pre-culturing a target cell is not particularly limited, and examples of the method include a method for culturing an adherent cell in a cell culture container such as a petri dish or a plate and a method of culturing a floating cell with the floating cell suspended in a culture medium. The culture medium used for culture is not particularly limited as long as the culture medium is a culture medium usually used for the culture of a target cell. Examples of the culture medium include solid culture mediums such as an agar medium and liquid culture mediums such as Dulbecco's Modified Eagle Medium (DMEM), RPMI 1640 medium, or Glasgow Minimum Essential Medium (GMEM). In addition, the culture medium can contain a well-known additive. A feeder cell suitable for culture can also be used. Culture conditions such as culture time, culture temperature, and $CO_2$ concentration, can be set suitably.

Next, the pre-cultured liquid medium is removed. In the case of an adherent cell, the culture medium may be removed with an aspirator, etc. In the case of a floating cell, the target cell suspended in the culture medium is separated by operation such as centrifugal separation or filtration, and the culture medium is removed.

Next, a step of adding an introduction liquid containing a molecule of interest is performed. The introduction liquid is preferably added so as to cover the target cell thinly. When the target tissue is used instead of the target cell, a very small amount of the introduction liquid containing the molecule of interest is directly added to, for example, an excised tissue section or a tissue.

When the introduction liquid containing the molecule of interest is contacted with the target cell, it is possible to use, for instance, a procedure including dripping an introduction liquid containing a molecule of interest onto a target cell, or a procedure including mixing a target cell and an introduction liquid. In addition, as another procedure, it is possible to use a procedure including adding an introduction liquid containing a molecule of interest to a dispersion liquid or a suspension containing a target cell, etc.

<Step of Introducing Molecule of Interest>

Then, a step of introducing a molecule of interest is performed. It is preferable to introduce a molecule of interest by subjecting a target cell to creeping discharge or plasma treatment in the introduction process of the present invention. Since a reagent with cytotoxicity is not used for these methods, the methods enable suppression of cell death. Even though the vector is a high molecular weight vector wherein the gene introduction is generally difficult (for example, 5 kDa or more, preferably 10 kDa or more) in the introduction method by creeping discharge or plasma treatment, the introduction number of the molecule of interest per cell can be increased while high gene transfer efficiency can be maintained, and a transformed cell can therefore be obtained more efficiently than in methods that have been generally performed until now. Further, since the molecule of interest can be introduced by endocytosis without damaging a chromosome, the incorporation of the molecule of interest into a chromosome can be suppressed, and a cell in which the exogenous gene is not inserted into the chromosome can be obtained. For example, when a gene is introduced by electroporation, incorporation into a chromosome occurs in 40 to 90% of transformed cells of interest finally, and meanwhile, according to the present method, the rate can be significantly reduced to preferably 20% or less, more preferably 10% or less. Since the recombination of a chromosome, mutation, etc. that occur at random and spontaneously cannot be prevented even by the introduction method by creeping discharge or plasma discharge, a cell in which a exogenous molecule of interest is incorporated into a chromosome is rarely produced.

As a method for introducing a molecule of interest using creeping discharge, a method described in Japanese Patent Laying-Open No. 2010-220517 can be suitably used. As a method for introducing a molecule of interest using plasma treatment, a method described in WO 2002/064767, Japanese Patent Laying-Open No. 2013-255475, or Japanese Patent Laying-Open No. 2013-255474, etc. can be suitably used.

A general-purpose transfection reagent using endocytosis (for example, a lipofection reagent) can also be used for the introduction liquid. In this case, in a process of introducing a molecule of interest, creeping discharge or plasma treatment can also be used in combination, or may not be used in combination.

[Creeping Discharge]

A method for introducing a molecule of interest using creeping discharge will be described in detail hereinafter. The method for introducing a molecule of interest using creeping discharge comprises the above step of contacting an introduction liquid containing a molecule of interest with a target cell and a step of applying electric discharge to the target cell and the introduction liquid from a plurality of electrodes provided away from the introduction liquid.

<Step of Applying Electric Discharge to Target cell and Introduction Liquid>

The number of the electrodes in the step of applying electric discharge to the target cell and the introduction liquid is not particularly limited, and electric discharge is applied to the introduction liquid from a plurality of electrodes provided away from the introduction liquid containing the molecule of interest. For example, current flows in the introduction liquid or on its surface layer, or an electric field is generated thereby. The present step preferably comprises a step of installing a plurality of electrodes in a region in which the introduction liquid containing the molecule of interest can be subjected to electric discharge, a step of applying voltage between the plurality of electrodes, and a step of generating electric discharge between the plurality of electrodes and the introduction liquid containing the molecule of interest. The molecule of interest is introduced into the target cell by these steps.

In the step of installing electrodes, a plurality of electrodes are preferably installed in a region in which electric discharge can be applied to the introduction liquid with the target cell and the introduction liquid containing the molecule of interest held in a cell culture container such as a petri dish.

Here, as long as the above container has a structure in which the target cell and the introduction liquid containing the molecule of interest can be held, the container is not particularly limited. Examples of the container include a plate, a petri dish, a tube, a test tube, and a flask.

In the step of applying (supplying) voltage between the plurality of electrodes, a voltage of preferably around several kVpp to several tens of kVpp, more preferably 1 kVpp to 30 kVpp, and further preferably 3 kVpp to 10 kVpp, is applied between the plurality of electrodes. When a voltage higher than several tens of kVpp is applied, the death rate of the target cell increases. Meanwhile, the effect of improving the introduction rate of the molecule of interest cannot be obtained at a voltage lower than several kVpp.

The step of generating electric discharge from the plurality of electrodes is a step achieved almost simultaneously by the above step of supplying voltage between the plurality of electrodes. Performing electric discharge between the electrodes provided away from the introduction liquid containing the molecule of interest, and the introduction liquid containing the molecule of interest by such voltage application enables the introduction of the molecule of interest to be achieved.

The electric discharge time is preferably 0.1 msec to 100 msec, more preferably 0.5 msec to 20 ms, and further preferably 1 msec to 5 msec. When current flows for a longer period of time than 100 msec, the death rate of the target cell increases. Meanwhile, the effect of improving the introduction rate of the molecule of interest cannot be fully obtained at a current conducted for a shorter period of time than 0.1 msec.

To obtain the transformed cell of interest, it is preferable that the voltage be higher, and the electric discharge time be longer than when the molecule of interest is usually introduced. Although the cytotoxic effects of the target cell are great, the number of cells into which the molecule of interest is introduced can be increased, and the amount of the molecule of interest introduced per cell can be increased. Therefore, the production efficiency of the transformed cell can be increased.

<Introduction Device for Creeping Discharge>

FIG. 1 shows an example of an introduction device for creeping discharge. The introduction device comprises two needlelike electrodes 1, a power source (voltage supply means) 2, and a container 3. Voltage can be applied between the two electrodes with power source 2. The structure of the introduction device is not limited to the structure shown in FIG. 1.

The plurality of electrodes 1 that the introduction device described in FIG. 1 comprises are provided away from an introduction liquid 5 containing a molecule of interest. Performing electric discharge between the electrodes and the introduction liquid containing the molecule of interest by applying voltage between the plurality of electrodes introduces the molecule of interest into a cell.

The introduction device is characterized in that the plurality of electrodes 1 are separated and installed above introduction liquid 5 containing the molecule of interest in contact with target cell 4 in a method for introducing the molecule of interest of the present invention. In FIG. 1, electrodes 1 are provided away from introduction liquid 5 containing the molecule of interest. When electrodes 1 generate electric discharge 6 between electrodes 1 and introduction liquid 5 containing the molecule of interest, the molecule of interest is introduced between the electrodes. Electrodes 1 and introduction liquid 5 containing the molecule of interest are installed so that the shortest distance between them is 10 mm or less, and they are out of contact. The distance between electrodes 1 and introduction liquid 5 containing the molecule of interest is preferably 0.1 to 5 mm, and further preferably 0.5 mm to 1 mm. Thus, installing electrodes 1 and introduction liquid 5 containing the molecule of interest out of contact with each other causes suitable electric discharge.

Furthermore, in the present invention, it is preferable to adjust the distance between the plurality of electrodes and the voltage applied between the electrodes so that plasma discharge does not occur between the electrodes directly. It is because when plasma discharge occurs between the electrodes, plasma at atmospheric pressure is unstable, charging in the introduction liquid containing the molecule of interest is therefore unstable, and the introduction efficiency of the molecule of interest, etc. are unstable. Preferable ranges of the distance between such a plurality of electrodes and the voltage applied between the electrodes are influenced by the electrical resistance of the introduction liquid containing the molecule of interest, etc., and cannot be unconditionally determined. However, when an aqueous solution containing a usual molecule of interest is used, the distance between any two pairs of electrodes is preferably 10 to 100 mm, and the voltage applied between any two pairs of electrodes is preferably 1 to 30 kV among the plurality of electrodes.

The voltage supply means that supplies, to the above electrodes, voltage for subjecting the introduction liquid containing the above molecule of interest to electric discharge from the above electrodes is not particularly limited, and examples of the voltage supply means include a power source supply device such as a high voltage power source, FP1000 (manufactured by PEARL KOGYO Co., Ltd.). Any of a sine wave, half-wave rectification, full-wave rectification, and a pulse can be used for a waveform supplied to the electrodes.

Although the shape of the electrodes used for the introduction device of the present invention is not particularly limited, the shape of the electrodes is preferably a shape such as a needle shape in which the tip is on the side of introduction liquid 5 containing the molecule of interest so that it is not necessary to apply voltage higher than necessary to perform electric discharge on the introduction liquid containing the molecule of interest from the electrodes. The material of the electrodes is not particularly limited, examples of the material include tungsten and molybdenum, and the material is preferably a material that does not easily corrode or a material such as gold, silver, and platinum having bactericidal effects.

The number of the electrodes used for the introduction device is not limited to two, and the number of the electrodes is preferably two or more. When the number of the electrodes is two or more, the introduction can be uniformed without needing operation such as sample rotation, the introduction rate of the molecule of interest further improves, and the death rate of the target cell is also reduced.

The number of the electrodes used for the introduction device may be determined so that the numbers of positive electrodes and negative electrodes are the same, or the numbers of positive electrodes and negative electrodes are different.

When the plurality of electrodes are disposed, it is preferable to provide resistors 22 between power source 2 and electrodes 1 so that current does not converge on specific electrodes, and uniform introduction of the molecule of interest is not prevented and to perform adjustment so that current flows uniformly. Coils, capacitors, etc. may be used instead of resistors 22.

The structure of the present introduction device is not limited to the structure described in the present embodiment. As long as the same effect as that of the present embodiment is obtained, for example, the numbers and the installation forms of the electrodes may be different shapes from each other. Power source 2 preferably comprises a rectifier.

According to the present method, since the spray of gas, etc. are not necessary, the target cell is less likely to dry, and addition of an extra buffer solution, etc. is unnecessary. In addition, the treatment in a short time is enabled, and special electrode configuration is not necessary, either, and simplification can be achieved.

[Plasma Treatment]

A method for introducing a molecule of interest using plasma treatment will be described in detail hereinafter. The method for introducing a molecule of interest using plasma treatment comprises the above step of contacting the introduction liquid containing the molecule of interest with the target cell and a step of contacting a mixture comprising one or more selected from the group consisting of a charged particle, an excited atom, and an excited molecule with the introduction liquid and the target cell.

<Step of Contacting Mixture Comprising One or More Selected from Group Consisting of Charged Particle, Excited Atom, and Excited Molecule with Introduction Liquid and Target Cell>

In the present step, for example, the introduction liquid containing the molecule of interest and the target cell are irradiated with a mixture, namely plasma, from a top fine electrode. In the present step, the position of the top fine electrode is first adjusted at a desired position in the introduction liquid. A bottom electrode may be installed on the opposite side of a container storing the target cell to the top fine electrode. Then, voltage is applied on the top fine electrode to generate plasma. When a top fine electrode having an ejection port in the shape of a hollow pipe is used, a mixture precursor may be ejected from the ejection port to the introduction liquid and the target cell.

The mixture precursor is a precursor for generating a mixture comprising one or more selected from the group consisting of a charged particle, an excited atom, and an excited molecule. Examples of the mixture precursor include gas containing one or more selected from the group consisting of air, nitrogen gas, oxygen gas, carbon dioxide gas, helium gas, neon gas, argon gas, krypton gas, and xenon gas. The combination of gases is not limited to these, and the precursor may contain a solid or a liquid. For example, applying voltage on the mixture precursor generates a mixture having one or more selected from the group consisting of a charged particle, an excited atom, and an excited molecule as a component. The mixture may be generated by giving energy to the mixture precursor, and a method for giving energy may not be voltage application.

The mixture precursor is fed to the inner pore of the top fine electrode at a predetermined flow rate with a mixture precursor feeder connected with the inner pore of the top fine electrode in the shape of a hollow pipe and ejected from the ejection port, for example. The outer diameter of the top fine electrode is preferably 1 mm or less, and more preferably 100 μm or less. The amount of the mixture precursor ejected per the top fine electrode is preferably 100 sccm or less.

Next, applying voltage between the top fine electrode and the bottom electrode generates a mixture from a mixture precursor (for example, He gas). When this mixture (mixture comprising one or more selected from the group consisting of a charged particle, an excited atom, and an excited molecule) contacts with the introduction liquid and the target cell and has an effect on the introduction liquid and the target cell, the molecule of interest is introduced into the target cell.

In the step of applying voltage, the applied voltage is preferably around several kV to several tens of kV, more preferably 2 kV to 30 kV, and further preferably 5 to 20 kV. When current flows at a voltage higher than several tens of kV, the death rate of the target cell increases. Conversely, when current flows at a voltage lower than several kV, the effect of improving the introduction rate of the molecule of interest cannot be obtained.

The step of generating a mixture is a step achieved almost simultaneously by the above step of applying voltage. When the mixture (mixture comprising one or more selected from the group consisting of a charged particle, an excited atom, and an excited molecule) thus has an effect on the liquid containing the molecule of interest (introduction liquid) and the target cell, the introduction rate of the molecule of interest can be improved remarkably, and the death rate of the target cell can be reduced markedly.

Time for which voltage is applied is preferably 0.1 msec to 100 msec, more preferably 0.5 msec to 50 msec, and further preferably 1.0 msec to 20 msec. When voltage is applied for a longer period of time than 100 msec, the death rate of the target cell increases. Meanwhile, the effect of increasing the introduction rate of the molecule of interest cannot be fully obtained by application for a shorter period of time than 0.1 msec.

According to the present introduction method, a cell can be made to express a protein of interest efficiently, and the protein of interest can be made to exist stably. A transformed cell can be established efficiently thereby, and its effect can be produced in the health maintenance of an individual animal body, improvement in a physical constitution, the prevention of disease, etc. by improvement in cell function. The present introduction method is not limited to the uses described in the present embodiments and Examples, and can be used for conferring a function on a cell.

<Introduction Device for Plasma Discharge>

Although an example of an introduction device for plasma discharge will be described hereinafter, the structure of the introduction device is not limited to this. The introduction device of the molecule of interest by plasma discharge has a structure and a function used suitably for the above method for introducing a molecule of interest, and preferably comprises a container, a top fine electrode provided on the opening side of the container and away from the introduction liquid, voltage supply means (power source), and a bottom electrode provided on the opposite side of the container to the top fine electrode. Predetermined voltage can be applied between the top fine electrode and the bottom electrode by the voltage supply means. When the top fine electrode in the shape of a hollow pipe is used, it is preferable that the electrode comprise a mechanism for ejecting a mixture precursor.

The voltage supply means comprises a signal generator, a linear amplifier, a matching circuit, and a boosting transformer. The voltage supply means is not particularly limited, and examples of the voltage supply means include a power source supply device such as a high voltage power source, FP1000 (manufactured by PEARL KOGYO Co., Ltd.). Any of a sine wave, half-wave rectification, full-wave rectification, and a pulse can be used for a waveform supplied to the electrodes.

The introduction device basically comprises a power source (voltage supply mechanism), electrodes, and conductive wire connecting the power source and the electrodes. The power source comprises a signal generator, a linear amplifier, a matching circuit, a boosting transformer, etc., those are mutually electrically connected with the top fine electrode or the bottom electrode by the conductive wire, and parameters such as inter-electrode voltage, electrode distance, frequency, a pulse period (pulse frequency), and duty can therefore be set as various conditions. Mixtures having various properties can be generated thereby. A connection circuit connecting the power source supply means with an electrode (the top fine electrode or the counter electrode) preferably has a rectifier, a resistor, a coil, or a capacitor.

In the introduction device, the above parameters such as inter-electrode voltage, electrode distance, frequency, a pulse period, and duty can be changed so that conditions of the mixture with which a target cell is irradiated can be changed depending on the type of the target cell, and the type of the molecule of interest.

The shape of the top fine electrode is preferably needle-like. The material of the top fine electrode and the bottom electrode is not particularly limited, examples of the material include tungsten and molybdenum, and the material is preferably a material which does not easily corrode and a material such as gold, silver, and platinum having a bactericidal effect.

In the present invention, moving up and down a single or a plurality of top fine electrodes in the perpendicular direction enables adjustment of the range of the target cell into which the molecule of interest is introduced. For this reason, the shortest distance between the top fine electrode and the introduction liquid and the target cell is preferably set as 5 mm or less.

The number of the top fine electrode may be one or more. When the introduction device comprises many top fine electrodes, the molecule of interest can be simultaneously introduced into many target cells. The molecule of interest can be introduced into a wide range of target cells with many top fine electrodes.

The container that stores the introduction liquid and the target cell may have a single or a plurality of sample holders for holding this target cell, and a single or a plurality of top fine electrodes are installed at the positions corresponding to these sample holders in this case.

The introduction device preferably includes a vertical driving mechanism that drives the top fine electrode and the container up and down relatively. That is, the introduction device preferably includes the position adjustment means of the storing container of the introduction liquid and/or the position adjustment means of the top fine electrode. The distance between the top fine electrode and the introduction liquid can be optimized thereby.

[Post-Culture Process]

The production method of the present invention preferably includes a process of post-culturing the target cell after the above introduction process. In the post-culture process, the target cell into which the molecule of interest is introduced is cultured, for example, for 4 hours or more and 2 months or less, preferably for 3 days or more and 1 month or less from the introduction. It is preferable to perform suitable culture medium exchange every several days meanwhile. Culture conditions such as culture temperature and $CO_2$ concentration can be set suitably.

In the post-culture process, the culture medium for the target cell preferably contains a selective molecule. The selective molecule is not particularly limited as long as the selective molecule is a molecule that eliminates a cell into which the molecule of interest is not introduced by the suppression of cell proliferation, the promotion of cell death, or the induction of apoptosis, etc. Since only a cell into which the molecule of interest is introduced can be selected and cultured thereby, the production efficiency of a transformed cell of interest can be improved. For example, when the below-mentioned antibiotic resistance genes are contained as the molecule of interest, neomycin, the neomycin analog G418, hygromycin, puromycin, blasticidin, other antibiotics, etc. can be used as the selective molecule. The concentration of the selective molecule and the culture time vary depending on the cell. For example, when a human dermal fibroblast HDF cell is subjected to selective culture with G418, it is preferable to culture the cell for 1 to 3 days at a concentration of 100 to 1000 µg/mL. It is because when the selective molecule is added over a long period of time, a possibility that the cell in which the molecule of interest is incorporated into a chromosome of the target cell is selected increases. When the introduction efficiency of the molecule of interest is more than 80%, the cell may not be cultured in the presence of the selective molecule.

The molecule of interest preferably comprises a selective marker molecule having resistance to the selective molecule. The selective marker molecule is a molecule for screening a target cell into which the molecule of interest is introduced. Examples of the selective marker molecule include a neomycin resistance gene, a puromycin resistance gene, and a blasticidin resistance gene. The selective marker molecule may be inserted into the same vector as a vector into which a gene that confers, deletes, or maintains a trait on/in the target cell is inserted. In this case, the target cell into which the molecule of interest is introduced can be selected more appropriately. When the selective marker molecule is inserted into a different vector from the vector into which a gene that confers, deletes, or maintains a trait on/in the target cell is inserted, fully reducing the amount of the vector into which the selective marker molecule is inserted based on that of the vector into which a gene that confers, deletes, or maintains a trait is inserted (for example, at a weight ratio of 10:1) and introducing both vectors enable sorting of the target cell in which the introduction of the vector into which a gene that confers, deletes, or maintains a trait on/in the target cell is inserted is supposed.

[Isolation Process of Transformed Cell]

The production method of the present invention preferably includes an isolation process of a transformed cell. In the present process, the target cell into which the molecule of interest is introduced or the post-cultured cell is cloned. A method well-known to those skilled in the art can be used as a monocloning method, and a cell can be cloned, for example, by limiting dilution, and picking up a single colony. When the transformed cell of interest can be determined by its morphology, the cell of interest determined visually can be picked up. It can be confirmed by a well-known method whether the isolated cell has obtained the trait of interest.

EXAMPLES

Hereinbelow, the invention will be described in more detail with reference to Examples. However, the invention is not limited to them.

Test Example 1: Introduction of Macromolecule into Cell

To establish a transformed cell such as an iPS cell efficiently, an episomal plasmid having 10 kbp or more (around 7 million Da or more) is desirably introduced. Low introduction efficiency of a macromolecule contributes to low production efficiency of an iPS cell. Then, the introduction efficiency of a macromolecule using creeping discharge was verified.

Figure 2:
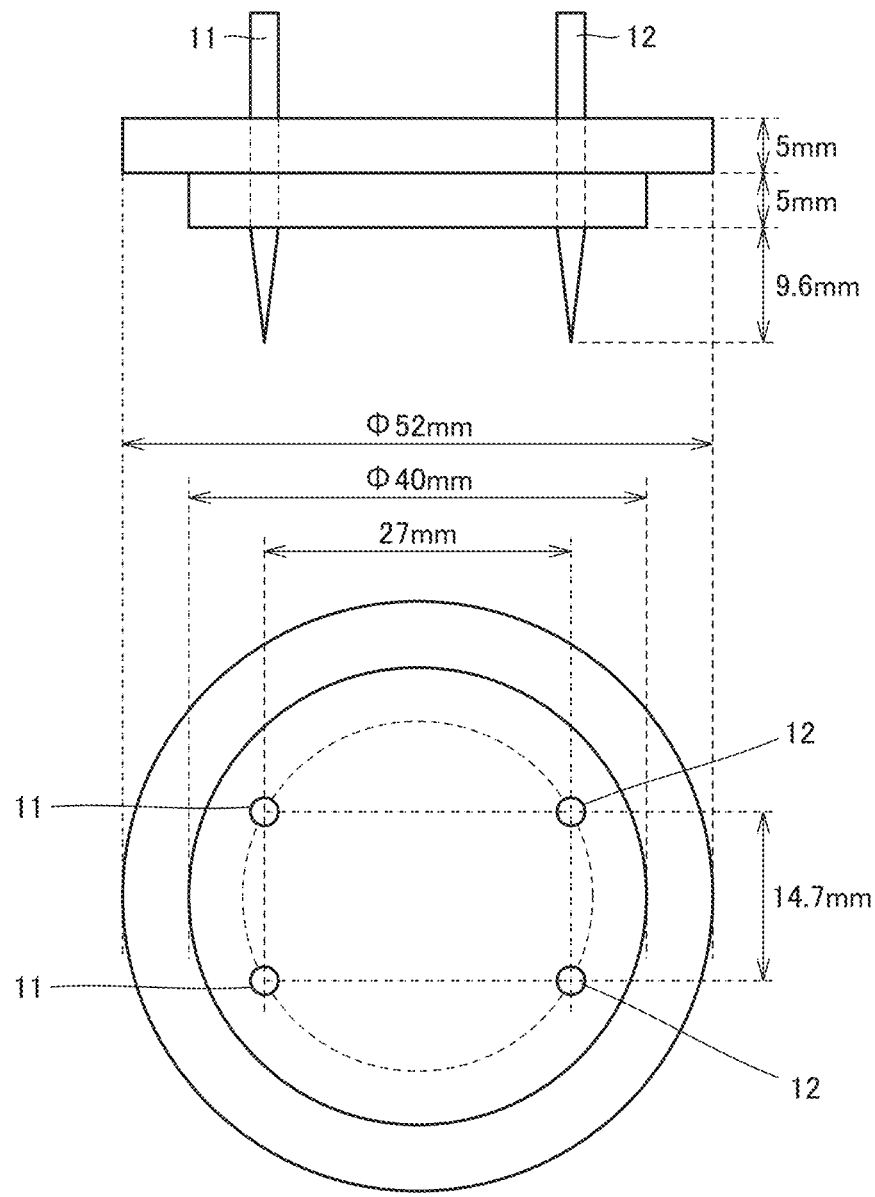
FIG. 2 is a schematic side view and a top view describing a portion of a device used for introducing a molecule of interest of Example 1.

In Test Example 1, a gene was introduced by creeping discharge using the introduction device shown in FIG. 1. In the case of plasma treatment using a single top fine electrode, the discharge range was small, and the number of cells into which a gene could be introduced was few. In the present Test Example, the gene introduction into a large amount of cells was therefore attempted using creeping discharge. A 3.5-cm plastic petri dish was used for the container of the present Test Example, and human dermal fibroblast HDF cells were used as target cells. As shown in FIG. 2, in the present Test Example, an introduction device in which two positive electrodes 11 and two negative electrodes 12 were disposed, and a total of four electrodes were disposed was used. The distance between a positive electrode and a negative electrode is around 27 mm.

Figure 3:
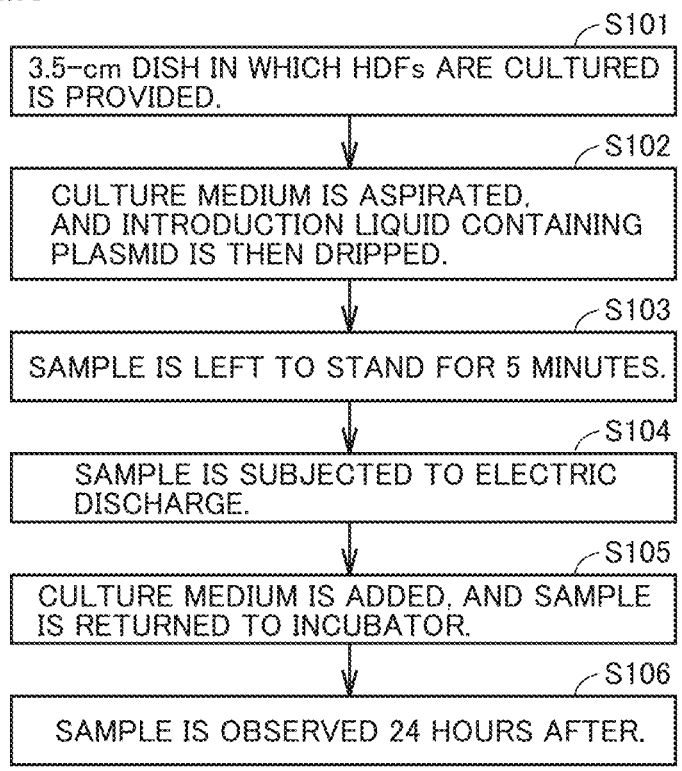
FIG. 3 is a flow chart describing a method for introducing a molecule of interest into a target cell in Test Example 1.

The procedure of the present Test Example will be described using FIG. 3. First, 2 mL of D-MEM high glucose medium (FUJIFILM Wako Pure Chemical Corporation: 045-30285) was added to the 3.5-cm plastic petri dish subjected to coating treatment with laminin. Human dermal fibroblast HDF cells were inoculated at around $3.0\times10^5$ cells/petri dish, and the cells were cultured in a $CO_2$ incubator for 24 hours (S101 in FIG. 3). The culture medium was removed with an aspirator, and 120 μL of an introduction liquid containing 120 μg of pCXLE-EGFP (10.9 kbp) and 12 μg of pmCherry-C1 (4.7 kbp) (salt concentration: 0.05% by mass) was dripped (S102 in FIG. 3). The mixture was left to stand for 5 minutes at room temperature after dripping (S103 in FIG. 3), the petri dish was set in a creeping discharge device, and electric discharge was performed (S104 in FIG. 3). The applied voltage was 5.2 kV (half-wave rectification), the power source frequency was 20 kHz, and the voltage application time was 2 msec×2 times (interval 30 seconds). Then, 2 mL of a culture medium was immediately added, and the petri dish was returned to the $CO_2$ incubator, and the cells were cultured for 24 hours (S105 to 106 in FIG. 3).

Figure 4:
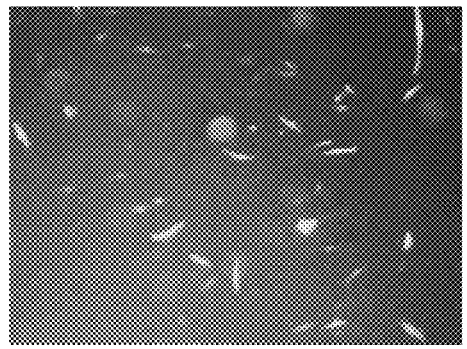
FIG. 4 is fluorescence photomicrographs showing that HDF cells cotransfected with the plasmids pCXLE-EGFP and pmCherry-C1 by creeping discharge express (A) GFP and (B) mCherry in Test Example 1.
Figure 4:

The HDF cells 24 hours after introduction were observed under a fluorescence microscope. FIG. 4(A) shows cells expressing GFP, and FIG. 4(B) shows cells expressing mCherry. Although it was generally difficult for a plasmid having a large size to be introduced into a cell, it was found that the large plasmid having around 10.9 kbp (7 million Da or more) could be introduced into a target cell in creeping discharge.

Test Example 2: Production of Transformed Cell

To the 3.5-cm plastic petri dish subjected to coating treatment with laminin was added 2 mL of D-MEM high glucose medium (FUJIFILM Wako Pure Chemical Corporation: 045-30285). Human dermal fibroblast HDF cells were inoculated at around $3.0\times10^5$ cells/petri dish, and the cells were cultured in a $CO_2$ incubator for 24 hours. The culture medium was removed with an aspirator, and 120 μL of a plasmid solution listed in Table 1 was dripped. The mixture was left to stand at room temperature for 5 minutes, the 3.5-cm plastic petri dish was then set in the creeping discharge device, and electric discharge was performed at 3.9 kV for 2 msec. The creeping discharge device that was the same device as in Test Example 1 was used. Then, 2 mL of a culture medium was immediately added, the petri dish was returned to the $CO_2$ incubator, and the cells were cultured for 24 hours. The cells after culture were observed under a microscope, cells into which a selective marker was introduced were confirmed, 2 mL of D-MEM high glucose medium containing 100 to 1000 μg/mL G418 was added to the cells, and then the cells were cultured for 24 hours to 72 hours.

TABLE 1

Table 1 Type and amount of plasmid

| Plasmid name | Introduced gene | Plasmid size | Amount added |
|---|---|---|---|
| pCXLE-hSK | SOX2 and KLF4 | 12.7 kbp (7.92 million Da) | 30 μg |
| pCXLE-hUL | L-Myc and Lin28 | 12.1 kbp (7.52 million Da) | 30 μg |
| pCXLE-hOCT3/4-shp53-F | hOCT3/4 | 11.7 kbp (7.29 million Da) | 30 μg |
| pCXLE-FLAG-TET1 | Tet1 | 16.7 kbp (10.43 million Da) | 30 μg |
| pmCherry-C1 | mCherry | 4.7 kbp (2.95 million Da) | 12 μg |

Figure 5:
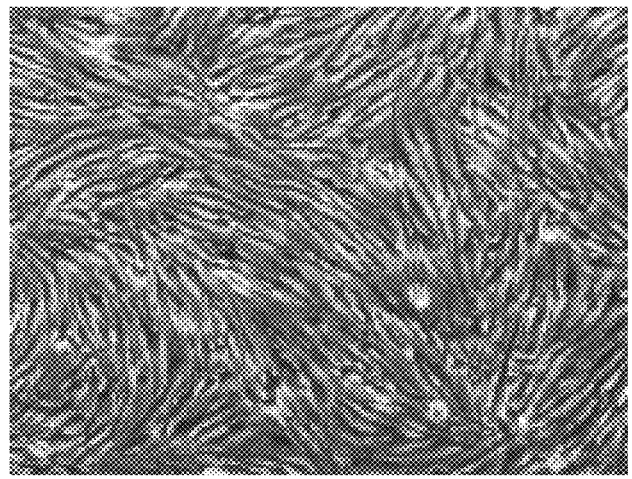
FIG. 5 is bright field photomicrographs of (A) HDF cells before the introduction of a molecule of interest and (B) iPS cells after the introduction.
Figure 5:
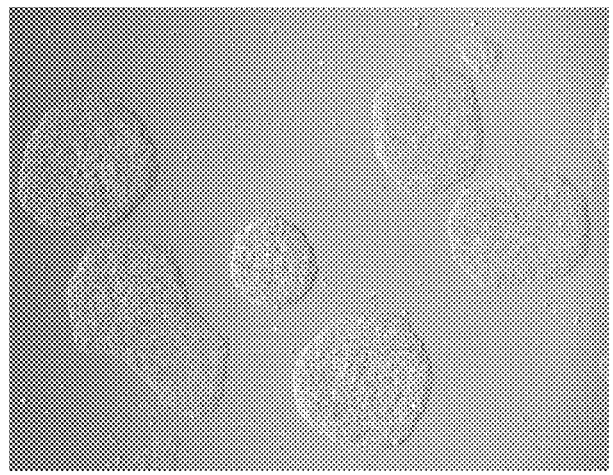

The D-MEM high glucose medium containing G418 was removed, 2 mL of Essential 8 Medium (Thermo Fisher Scientific K.K., Invitrogen: A1517001) was added, and the cells were cultured in the $CO_2$ incubator. The culture medium was exchanged every 2 to 3 days, and the culture was continued for 3 to 4 weeks. FIG. 5 (A) shows the HDF cells before plasmid introduction. iPS-like cells shown in FIG. 5 (B) appeared 3 to 4 weeks after the plasmid was introduced. The reprogramming cells after plasmid introduction had a different morphology from that of original HDF cells, and exhibited a morphology typically seen in iPS cells (for example, a colony with a dome-likeshape, a boundary smooth surface, and/or gleamed whitishly). The iPS cells that appeared were picked up, passage was performed in a 3.5-cm plastic petri dish subjected to coating treatment with laminin, and a single colony that proliferated was freeze-preserved.

<Method for Confirming Whether Molecule of Interest Remains by qPCR and Results>

Some of iPS cells collected at the time of freeze preservation were washed with PBS (NACALAI TESQUE, INC., cat. No. 14249-24) and centrifuged. PBS was removed with an aspirator, and the cell pellet was stored at −80° C.

The frozen cell pellet was suspended in 200 μL of PBS at room temperature. The genome DNA of the cells was extracted using the genome DNA extraction kit: DNeasy Blood & Tissue kit (QIAGEN K.K.—Japan, cat. No. 69504) according to the protocol. Specifically, 20 μL of attached protease K was added, and the mixture was lightly mixed with a vortex mixer (Scientific Industries, Inc., Digital Vortex-GENIE 2) to be uniformly mixed. The mixture was spun down and left to stand at room temperature for 5 minutes. Then, 4 μL of optional RNase A (QIAGEN K.K.—Japan, cat. No. 19101) was added, and the mixture was lightly mixed with the vortex mixer to be uniformly mixed. The mixture was spun down with a desk centrifuge (Greiner Bio-One International GmbH, myFUGE mini centrifuge, C1008-B), and left to stand at room temperature for 2 to 5 minutes. 200 μL of a Buffer AL attached to the kit was added, and the mixture was immediately treated with the vortex mixer intermittently for 15 seconds. The mixture was spun down and incubated at 56° C. for 10 minutes with a heat block (ASTEC CO., LTD., Block Incubator BI-525). The mixture was spun down, 200 μL of 100% ethanol was added, and the mixture was immediately treated with the vortex mixer intermittently for 15 seconds. The mixture was spun down and lysate was poured into a QIAamp Mini spin column attached to the kit. The column was centrifuged (ThermoScientific, Sorvall ST8FR) at 6000 g and room temperature for 1 minute, and the lysate was passed through a column. The column was moved to a new 2-mL collection tube attached to the kit, and 500 μL of a Buffer AW1 was added. The collection tube was centrifuged at room temperature at 6000 g for 1 minute, and the lysate was passed through the column. The column was moved to a new 2-mL collection tube attached to the kit, and 500 μL of a Buffer AW2 was added. The collection tube was centrifuged at 20,000 g for 3 minutes at room temperature, and the column was moved to a new 2-mL tube (Eppendorf AG, Safe-Lock Tube). The 2-mL tube was centrifuged at 20,000 g for 1 minute at room temperature, and the column was moved to a new 1.5-mL tube (WATSON, 131-715C). Then, 100 to 200 μL of a Buffer AE was added, and the column was left to stand at 60° C. for 10 minutes. The tube was centrifuged at 6,000 g for 1 minute, and the genome DNA was extracted.

The genome DNA was quantified with a microspectrophotometer (Implen GmbH, NanoPhotometer P-Class), and was diluted with DDW to 10 ng/μL. qPCR was performed using 20 ng of the genome DNA per reaction. THUNDERBIRD SYBR qPCR mix (TOYOBO CO., LTD.) was used for a qPCR reagent. In a reaction system of 10 μL, 2 μL of 10 ng/μL genome DNA was used. Reaction was performed under the reaction conditions of 95° C.-60 seconds: 1 cycle and (95° C.-15 seconds and 60° C.-45 seconds): 40 cycles. A CFX96 real-time PCR analysis system (Bio-Rad Laboratories, Inc.) was used for an analysis system. qPCR was performed with a primer set for detecting an episomal vector and a primer set for detecting a CFTR gene of a chromosomal gene per cell strain. The cycle threshold (Ct) value of the episomal vector was corrected with Ct value of the CFTR gene (chromosomal gene). The primer sequences used are as follows.

For detecting an episomal vector (oriP) (Yu et al, Science, 324. 2009)
pEP4-SF1: TTCCACGAGGGTAGTGAACC
pEP4-SR2: CAGGCGAAGATTCAGGAGAG For detecting a CFTR gene (Uehara et al, Ann Clin Transl Neurol., 361-369. 2014)
CFTRexon24-F: GGCAGTACGATTCCATCCAG
CFTRexon24-R: GAAAGAGCTTCACCCTGTCG For a human iPS cell strain established in the present invention, it was confirmed whether the episomal vector (molecule of interest) remained. qPCR was performed on the same sample twice. The number of copies was calculated by doubling the relative amount of the episomal vector to CFTR, which is a chromosomal gene. Cell strains in which the ratio of the episomal vector/CFTR is 0.1 copies or less are defined as cells in which the molecule of interest does not remain.

Figure 6:
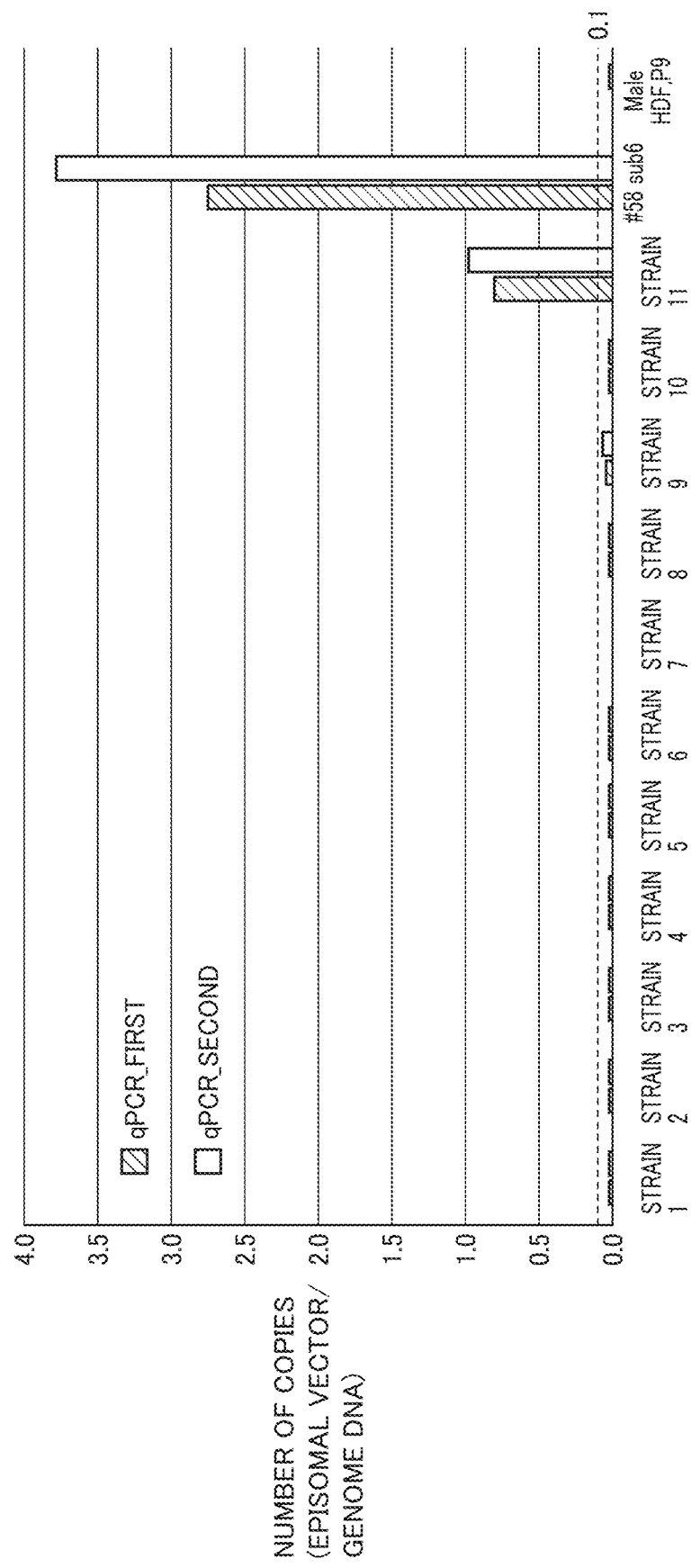
FIG. 6 is a graph obtained by measuring the number of copies of an episomal vector by qPCR. The relative amounts are shown with the amounts of the genome DNAs defined as 1.

FIG. 6 shows the results. Ten strains of the eleven examined strain (90.9%) have a ratio of the episomal vector/CFTR of 0.1 copies or less, and it is considered that the vector sequence is not incorporated into the genome DNA. For Strain 11 in which the vector sequence was detected, it is considered that the vector was incorporated by random incorporation that occurred at a low probability. Then, #58 sub6 was a cell strain in which the episomal vector was introduced by electroporation, and the vector was consequently inserted into the genome DNA, and was used as a positive control. As a negative control, the genome DNA of the human dermal fibroblast HDF cell (Male HDF, P9) used for establishing an iPS cell was used.

For the iPS cells produced by the introduction method of the present application and iPS cells established using a Nucleofector 2b (Lonza), which was an electroporator, the rates of cell strains in which the vector remained in the cells were compared. As shown in Table 2, the episomal vector residual ratios of the iPS cell strains established by creeping discharge exhibited noticeably low values as compared with the iPS cells established using the electroporator. The transformed cell in which the nucleic acid was not inserted into a chromosome could be obtained efficiently by the introduction method of the present application.

The residual amount of the episomal vector may also depend on the length of the culture period. However, the residual amounts of the episomal vector at the time of the production of frozen cell stocks were 0.1 copies or less in around 90% of the iPS cells produced using the present invention. These results show that the present invention is safe technology that is unlikely to cause the incorporation of the exogenous gene into a chromosome as compared with conventional methods.

[Table 2]

TABLE 2

Comparison of episomal vector residual rates by different methods for introducing gene

| Method for introducing gene | Vector residual rate |
| --- | --- |
| Creeping discharge | 9.1% |
| Electroporation | First: 40% |
|  | Second: 90% |

Test Example 3: Production of Transformed Cell

Figure 7:
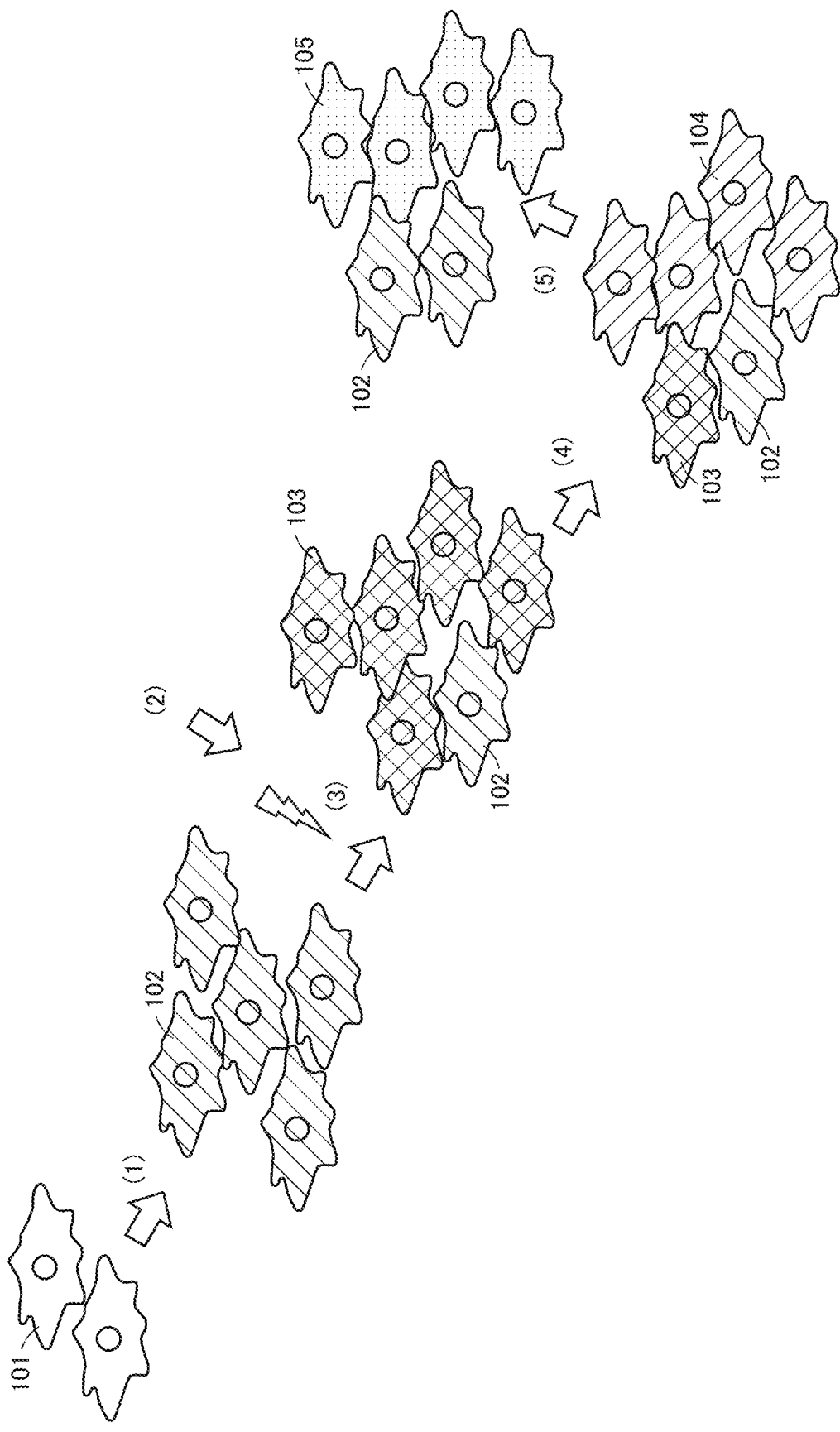
FIG. 7 is a schematic diagram describing Test Example 3.

In accordance with the method shown in FIG. 7, a target gene was knocked out using a genome editing system, genome editing was completed, and a transformed cell in which the genome editing system did not remain was then produced. According to this method, the knockout of a gene and the omission of a plasmid can be confirmed with fluorescence.

(1) A red fluorescence protein gene is integrated into the chromosome of cells 101 that do not exhibit fluorescence, and cells 102 that exhibit red fluorescence constantly (target cells) are established.

(2) A plasmid for genome editing having a sequence for knocking out red fluorescence protein and a gene sequence of green fluorescent protein (molecule of interest) is constructed.

(3) The constructed plasmid is introduced into cells 102 that exhibit red fluorescence. The cells into which the plasmid is introduced become cells 103 that exhibit red and green fluorescence.

(4) The cells into which the plasmid is introduced are cultured for around 2 weeks. When the red fluorescence protein gene is knocked out, the red fluorescence protein is gradually degraded, and cells 104 that exhibit only green fluorescence are produced.

(5) Culture is further continued. When the plasmid introduced into the cells degrades and is omitted, the cells do not exhibit green fluorescence, and transformed cells 105 in which the nucleic acid is not inserted into a chromosome can be produced.

The experiment actually performed will be described in detail hereinafter.

(1) Establishment of Cell Constantly Expressing mCherry Protein by Electroporation L-929 cells ($1\times10^6$ cells) were suspended in 90 µL of Opti-MEM, and 10 µL of a pmCherry-C1 plasmid (1 µg/µL) was added, and the mixture was mixed. The mixed liquid was poured into a cuvette for electroporation, an electroporator (NEPA21, Nepa Gene Co., Ltd.) was equipped with the cuvette, and application was performed under conditions in Table 3.

[Table 3]

TABLE 3

| Applicationion conditions of electroporator | | | | | |
|---|---|---|---|---|---|
| | Voltage (V) | Pulse width (ms) | Pulse interval (ms) | Number of times | Attenuation factor | Polarity |
| Poring Pulse | 180 | 1 | 50 | 2 | 10 | + |
| Transfer Pulse | 30 | 50 | 50 | 5 | 40 | +/− |

Figure 8:
FIG. 8 is (A) a fluorescence photomicrograph showing the expression of mCherry and (B) a bright field photomicrograph of L-929 cells into which a pmCherry-C1 plasmid is introduced by electroporation in Test Example 3.
Figure 8:
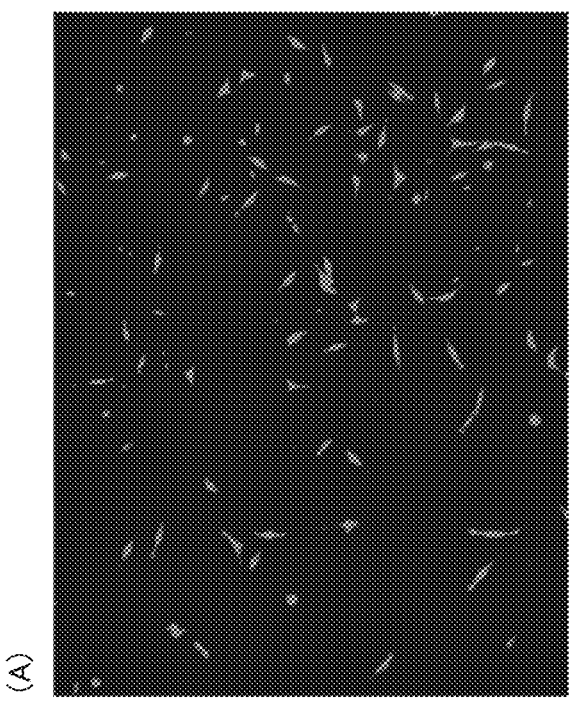
Figure 9:
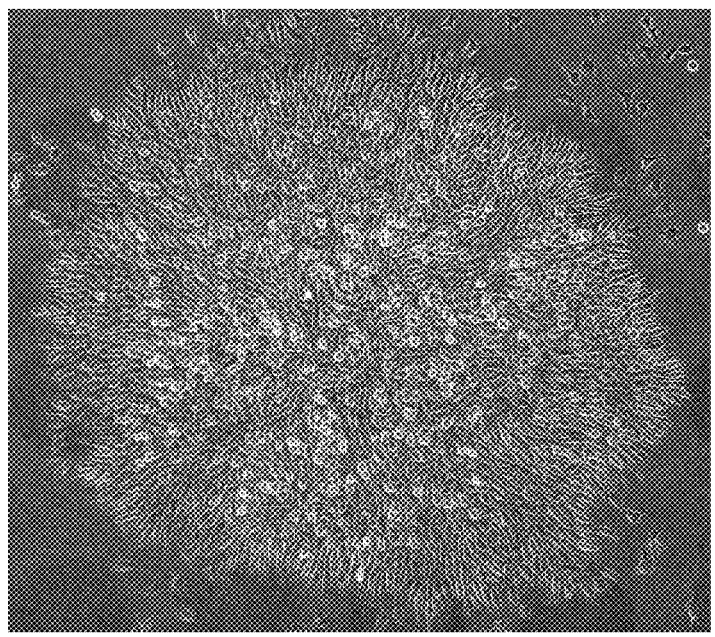
FIG. 9 is (A) a fluorescence photomicrograph showing the expression of mCherry and (B) a bright field photomicrograph of L-929-mCherry cells.
Figure 9:
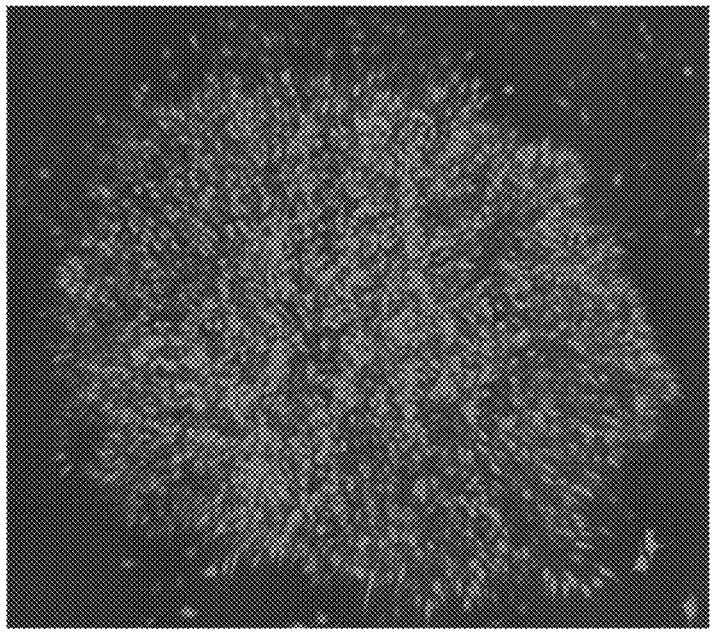

A reaction liquid containing the cells after application was suspended in 4.9 mL of MEM medium containing serum, the cells were inoculated on a 96-well plate in an amount of 100 µL, and the cells were cultured in a $CO_2$ incubator at 37° C. for 48 hours. The introduction efficiency of the pmCherry-C1 plasmid was 30%, and the cell survival rate was 65%. The cells were collected from the wells and cultured in 10 mL of MEM medium containing serum (containing 200 µg/mL of G-418) in a 10-cm petri dish for 1 month. FIG. 8 (A) shows cells that express mCherry and exhibit red fluorescence, and FIG. 8 (B) shows the cells under a bright field microscope. Then, a single colony of the L-929 cells into which the pmCherry-C1 plasmid was introduced was obtained by limiting dilution using a 96-well plate. The obtained single colony was suspended in 2 mL of MEM medium containing serum, and the cells were inoculated into a 3.5-cm petri dish and continuously cultured in a $CO_2$ incubator at 37° C. for 1 month. It was confirmed that a white clone (clone in which the mCherry gene was omitted) did not appear from the obtained colony (0.01% or less), and the cells were defined as constantly mCherry-expressing cells (L-929-mCherry cells) (FIGS. 9 (A) and (B)). It is considered that the pmCherry-C1 plasmid is inserted into the genome of the L-929-mCherry cells.

(2) Construction of Vector for Genome Editing

According to the manual attached to the kit, a vector for knocking out mCherry was constructed using a Guide-it CRISPR/Cas9 System (Clontech Laboratories, Inc.). A pGuide-it plasmid vector included in the kit has a ZsGreen1 gene that exhibits green fluorescence. The nucleotide sequences of primers for a guide RNA for knocking out the mCherry gene are as follows.

gRNA-1-Fwd: CCGGACCCAGACCGCCAAGCT-GAAGG gRNA-1-Rev: AAACCCTTCAGCTTGGCGGTCTGGGT

The nucleotide sequence of the vector for knocking out mCherry including the above guide RNA sequence was confirmed, and a plasmid psgRNA1-2 for genome editing holding a sequence of interest was obtained.

(3) Introduction of Plasmid psgRNA1-2 for Genome Editing

Figure 10:
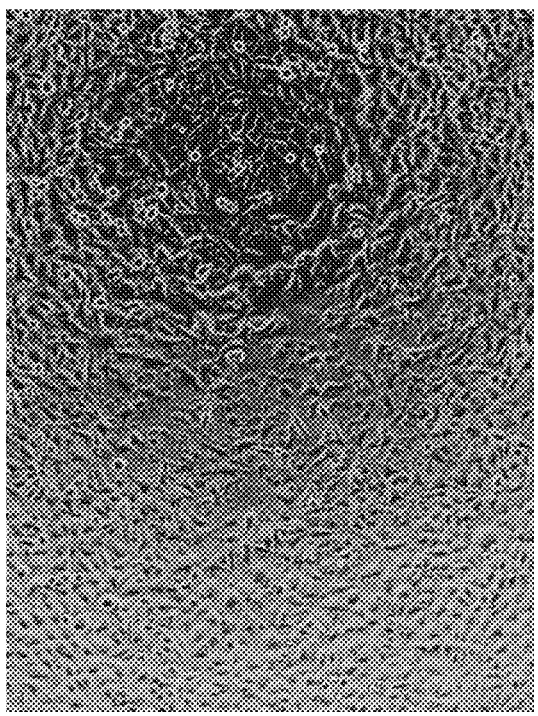
FIG. 10 is (A) a fluorescence photomicrograph showing the expression of mCherry, (B) a bright field photomicrograph, and (C) a fluorescence photomicrograph showing the expression of GFP of L-929-mCherry cells into which a psgRNA1-2 plasmid is introduced by plasma treatment.
Figure 10:
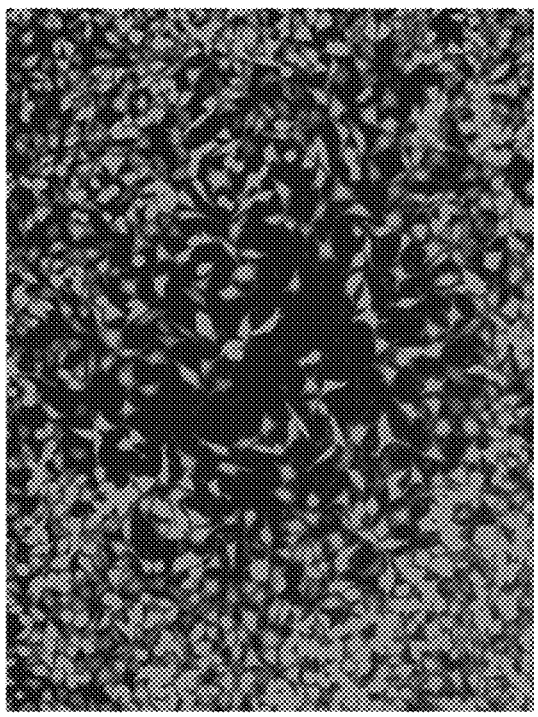
Figure 10:
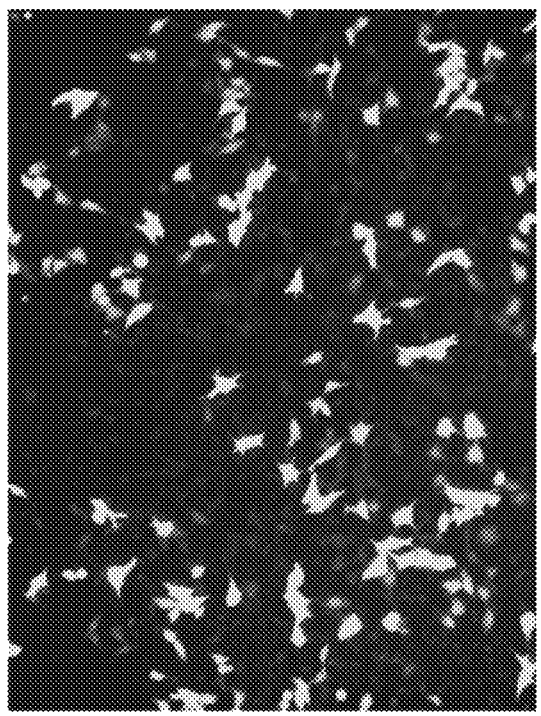

The L-929-mCherry cells ($1.3\times10^4$ cells) were inoculated on a 96-well plate and cultured in a $CO_2$ incubator at 37° C. for 24 hours. The culture medium was aspirated from the wells, 5 µL of a psgRNA1-2 plasmid (1 µg/µL) was added, and the cells were set in a plasma treatment device and irradiated with plasma under the conditions of 30 kV and 30 msec. The plasma treatment device that was the same device as a device described in Japanese Patent Laying-Open No. 2013-255475 was used. Then, 100 µL of the MEM medium containing serum was added after irradiation, and the cells were cultured in the $CO_2$ incubator at 37° C. for 48 hours. The L-929-mCherry cells exhibit red fluorescence constantly (FIGS. 10 (A) and (B)), and the cells into which the psgRNA1-2 plasmid was introduced also further exhibited green fluorescence (FIG. 10(C)).

(4) Knockout of mCherry Gene by Introduction of psgRNA1-2 Plasmid

Figure 11:
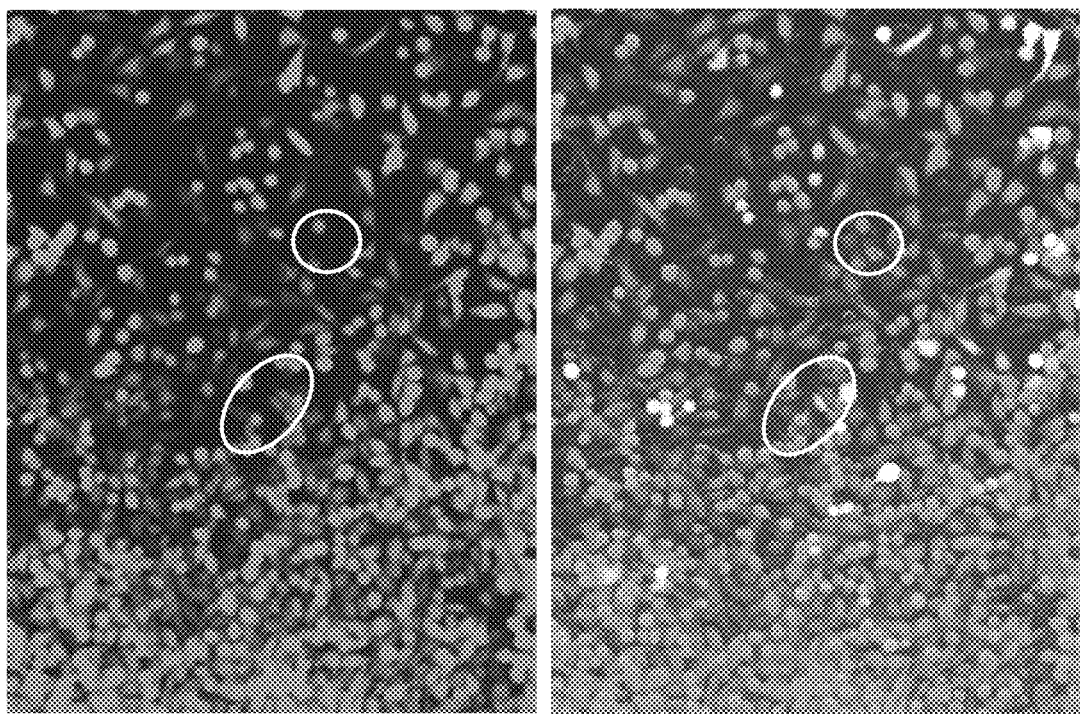
FIG. 11 is (A) a fluorescence photomicrograph showing the expression of GFP, (B) a fluorescence photomicrograph showing the expression of mCherry, (C) a bright field photomicrograph, and (D) a merged photograph thereof after L-929-mCherry cells into which a psgRNA1-2 plasmid is introduced by plasma treatment are cultured over a long period of time. Cells showing green fluorescence but not showing red fluorescence exist in circled portions in the figure.
Figure 11:
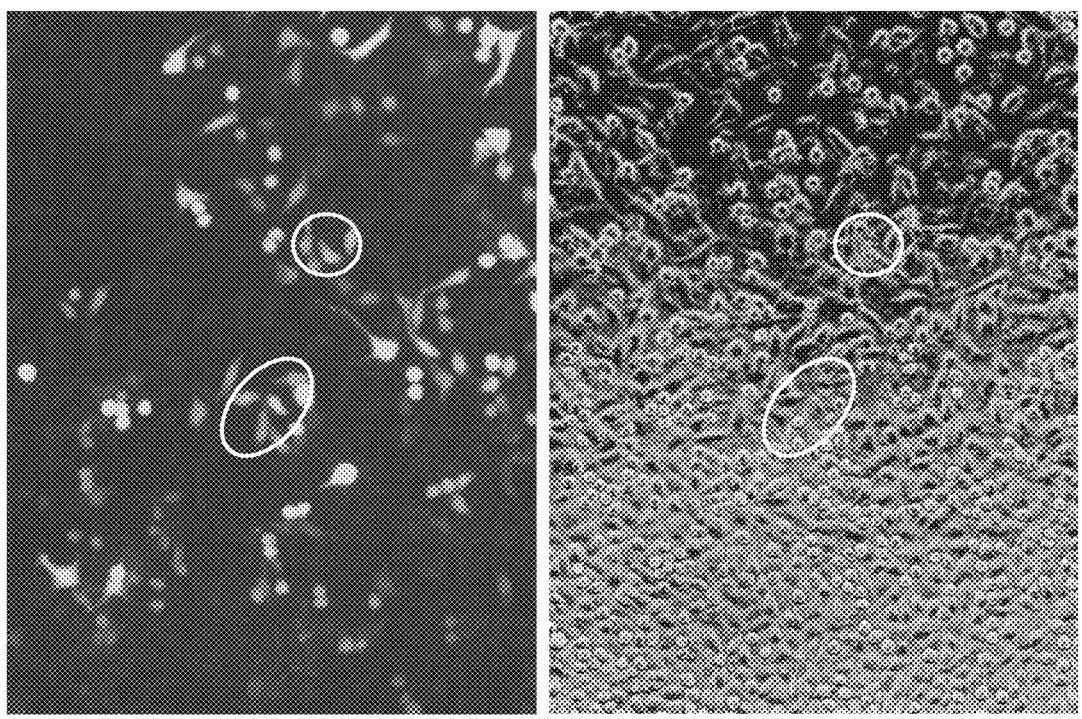

The cells were collected from the wells, inoculated into a 10-cm petri dish and cultured in a $CO_2$ incubator at 37° C. for 2 weeks. Consequently, some of cells that exhibited red and green fluorescence did not exhibit red fluorescence by introducing the psgRNA1-2 plasmid, and exhibited only green fluorescence (FIGS. 11 (A) to (D), the circled portions). Since the frequency of accidental gene mutation is generally as low as $1/10^5$, the fact that red fluorescence is not seen in a certain number or more of the cells suggests that the mCherry gene was knocked out with the genome editing system.

(5) Continuous Culture of Cells into which psgRNA1-2 is Introduced

A single colony of cells that exhibit green fluorescence was obtained by limiting dilution. When the obtained single colony was inoculated into a 10-cm petri dish and cultured in a $CO_2$ incubator at 37° C. for around 1 month, almost all of the cells that exhibited green fluorescence became cells that did not exhibit fluorescence. This suggests that the plasmid psgRNA1-2 for genome editing was omitted or degraded during cell proliferation without being incorporated into a genome.

The embodiments and Examples disclosed herein are examples regarding every point and should not be considered to be limited. The scope of the invention is defined by the CLAIMS but not the above description. Any modifications within the scope and the equivalent meaning of the CLAIMS are intended to be included.

INDUSTRIAL APPLICABILITY

A vector such as an introduced gene or a virus remains in a transformed cell to be used for regenerative medicine or gene therapy (for example, an iPS cell, a cell differentiated from an iPS cell, etc.), which has prevented the practical use of regenerative medicine or gene therapy in the past. Implementation in a high-level biohazard laboratory and highly skilled researchers have been required to obtain that transformed cell. According to the present invention, a molecule of interest can be conveniently introduced, a cell on/in which a trait is conferred or deleted can be consequently produced easily. Further, since the molecule of interest such as a exogenous gene is not held in the established cell, a probability that a conventional problem will occur is extremely low at the time of practical use. This enables research on analyzing an in vivo function of a specific molecule and application to broad fields including medicine, agriculture, and environment. The cell can be used, for example, for regenerative medicine, cell medicine, and gene therapy in the medical field and, for example, for breeding and selective breeding in the agricultural field or the environmental field.

REFERENCE SIGNS LIST

1: electrode, 11: positive electrode, 12: negative electrode, 2: power source, 22: resistor, 3: container, 4: target cell, 5: introduction liquid containing molecule of interest, 6: electric discharge, 101: cell that does not exhibit fluorescence, 102: cell that exhibits red fluorescence, 103: cell that exhibits red and green fluorescence, 104: cell that exhibits green fluorescence, 105: transformed cell.

The invention claimed is:

1. A method for producing transformed cells, comprising:
contacting an introduction liquid comprising a vector comprising a nucleic acid molecule of interest with a target cell to introduce the nucleic acid molecule of interest into the target cell,
wherein the vector is introduced via endocytosis into the target cell by creeping discharge or plasma treatment, and
the vector has a molecular weight from 2.95 million Da to 10.43 million Da.

2. The production method according to claim 1, wherein the vector expresses a protein that confers, deletes, or maintains a trait in the cell.

3. The production method according to claim 1, wherein the nucleic acid molecule is not inserted into a chromosome in 80% or more of the transformed cells.

4. The production method according to claim 1, comprising: culturing the target cell after the contacting.

5. The production method according to claim 4, wherein in the culturing, a culture medium for the target cell comprises a selective molecule that can kill a cell.

6. The production method according to claim 1, wherein the molecule of interest comprises a selective marker molecule having resistance to a selective molecule.

7. The production method according to claim 1, wherein the vector comprises one selected from the group consisting of a plasmid vector, a cosmid vector, a bacterial artificial chromosome (BAC), and a yeast artificial chromosome (YAC).

8. The production method according to claim 1, wherein the vector comprises one selected from the group consisting of pCLE-hSK, pCLE-hUL, pCLE-hOCT3/4-shp53-F, pCXLE-FLAG-TET1, and pmCherry-C1.

9. The production method according to claim 1, wherein the vector comprises one selected from the group consisting of a promoter sequence, a Kozak sequence, a Shine-Dalgarno sequence, an intron, a spacer sequence, an enhancer sequence, a terminator sequence, and an internal ribosome entry site (IRES).

10. The production method according to claim 1, wherein the vector is introduced by the endocytosis into the target cell by a lipofection reagent.

11. The production method according to claim 6, wherein the selective molecule comprises an antibiotic selected from the group consisting of neomycin, G418, hygromycin, puromycin, and blasticidin.

12. The production method according to claim 1, wherein the target cell comprises a cell selected from the group consisting of an epidermal cell, a mammary cell, a fat cell, a myoblast, an osteoblast, a hepatic cell, a cardiac muscle cell, a vascular endothelial cell, a B cell, a T cell, a monocyte cell, a neuron, including a pluripotent stem cell, a blood stem cell, a mesenchymal stem cell, a neural stem cell, and a tumor cell.

13. The production method according to claim 1, wherein the target cell comprises a target tissue selected from the group consisting of a viviparous tissue, an embryonic tissue, a skin tissue, a bone tissue, a cartilage tissue, a muscular tissue, a fat tissue, a cardiac muscle tissue, a nervous system tissue, a lung tissue, a pancreas tissue, a liver tissue, a hair papilla tissue, a dental pulp, and a tumor tissue.

14. The method according to claim 1, wherein the vector is introduced via endocytosis into the target cell by the creeping discharge.

15. The method according to claim 1, wherein the vector is introduced via endocytosis into the target cell by the plasma treatment.

16. The method according to claim 1, wherein the creeping discharge comprises applying voltage from 1 to 30 kV, or the plasma treatment comprises applying voltage from 2 to 30 kV.

17. The method according to claim 1, wherein an electric discharge time of the creeping discharge or the plasma treatment ranges from 0.1 msec to 100 msec.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: pEP4-SF1

<400> SEQUENCE: 1
ttccacgagg gtagtgaacc                                              20

<210> SEQ ID NO 2
<211> LENGTH: 20
<212> TYPE: DNA
<213> ORGANISM: Artificial Sequence
<220> FEATURE:
<223> OTHER INFORMATION: pEP4-SR2

<400> SEQUENCE: 2
caggcgaaga ttcaggagag                                              20

<210> SEQ ID NO 3
<211> LENGTH: 20
<212> TYPE: DNA
<213> ORGANISM: Artificial Sequence
<220> FEATURE:
<223> OTHER INFORMATION: CFTRexon24-F

<400> SEQUENCE: 3
ggcagtacga ttccatccag                                              20

<210> SEQ ID NO 4
<211> LENGTH: 20
<212> TYPE: DNA
<213> ORGANISM: Artificial Sequence
<220> FEATURE:
<223> OTHER INFORMATION: CFTRexon24-R

<400> SEQUENCE: 4
gaaagagctt caccctgtcg                                              20

<210> SEQ ID NO 5
<211> LENGTH: 26
<212> TYPE: DNA
<213> ORGANISM: Artificial Sequence
```

```
<220> FEATURE:
<223> OTHER INFORMATION: gRNA-1-Fwd

<400> SEQUENCE: 5
ccggacccag accgccaagc tgaagg                                          26

<210> SEQ ID NO 6
<211> LENGTH: 26
<212> TYPE: DNA
<213> ORGANISM: Artificial Sequence
<220> FEATURE:
<223> OTHER INFORMATION: gRNA-1-Rev

<400> SEQUENCE: 6
aaacccttca gcttggcggt ctgggt                                          26
```

UNITED STATES PATENT AND TRADEMARK OFFICE
CERTIFICATE OF CORRECTION

| | | |
|---|---|---|
| PATENT NO. | : 12,385,047 B2 | Page 1 of 1 |
| APPLICATION NO. | : 17/253867 | |
| DATED | : August 12, 2025 | |
| INVENTOR(S) | : Masafumi Jinno et al. | |

It is certified that error appears in the above-identified patent and that said Letters Patent is hereby corrected as shown below:

On the Title Page

Item (71), revise "I-GENE CORPORATION, Ehime (JP)" to, "I-GENE CORPORATION, Tokyo (JP)".

Signed and Sealed this
Eighteenth Day of November, 2025

John A. Squires
*Director of the United States Patent and Trademark Office*